United States Patent
Wilcox et al.

(10) Patent No.: US 10,524,898 B2
(45) Date of Patent: Jan. 7, 2020

(54) SELF-CENTERING PHAKIC REFRACTIVE LENSES WITH PARACHUTE DESIGN

(71) Applicant: MEDENNIUM, INC., Irvine, CA (US)

(72) Inventors: Christopher D. Wilcox, Mission Viejo, CA (US); Dimitrii Dementiev, Arese (IT); Jacob Feldman, Newport Beach, CA (US); Julian Abadia, Foothill Ranch, CA (US)

(73) Assignee: Medennium, Inc., Irvine, CA (US)

( * ) Notice: Subject to any disclaimer, the term of this patent is extended or adjusted under 35 U.S.C. 154(b) by 0 days.

(21) Appl. No.: 15/070,024

(22) Filed: Mar. 15, 2016

(65) Prior Publication Data

US 2016/0270906 A1    Sep. 22, 2016

Related U.S. Application Data

(63) Continuation-in-part of application No. 14/661,262, filed on Mar. 18, 2015, now abandoned.

(51) Int. Cl.
*A61F 2/16* (2006.01)
*A61F 9/008* (2006.01)

(52) U.S. Cl.
CPC ............ *A61F 2/1601* (2015.04); *A61F 2/161* (2015.04); *A61F 2002/1683* (2013.01); *A61F 2002/1689* (2013.01); *A61F 2009/00863* (2013.01)

(58) Field of Classification Search
CPC ........ A61F 2/1613; A61F 2/16; A61F 2/1648; A61F 2/1629; A61F 9/00781; A61F 2250/0015; A61F 2/161
See application file for complete search history.

(56) References Cited

U.S. PATENT DOCUMENTS

| | | | |
|---|---|---|---|
| 4,424,597 A * | 1/1984 | Schlegel | A61F 2/16 623/6.4 |
| 4,585,456 A | 4/1986 | Blackmore | |
| (Continued) | | | |

FOREIGN PATENT DOCUMENTS

| | | |
|---|---|---|
| CN | 201260732 Y | 6/2009 |
| CN | 203970615 U | 12/2014 |
| (Continued) | | |

OTHER PUBLICATIONS

Brubaker, R.F., "Flow of aqueous humor in human eyes", Invest Ophthalmol Vis Sci, 1 Dec., 1991, vol. 32, Issue 13, pp. 3145-66.
(Continued)

*Primary Examiner* — David H Willse
*Assistant Examiner* — Tiffany Shipmon
(74) *Attorney, Agent, or Firm* — Frost Brown Todd LLC

(57) ABSTRACT

An improved self-centering phakic refractive lens is disclosed. The lens floats freely in the posterior chamber of the eye and corrects vision of the patient but also prevents buildup of intraocular pressure, cataract induction and iris pigment dispersion. The lens comprises an optical body, haptic members which extend outward from the optical body, and a small hole in the approximate center of the optical body for the purpose of allowing aqueous humor to flow through that hole. The lens is designed such that its posterior surface conforms to the shape of the anterior surface of the patient's natural crystalline lens.

15 Claims, 5 Drawing Sheets

(56) References Cited

U.S. PATENT DOCUMENTS

| | | | |
|---|---|---|---|
| 5,258,025 A | | 11/1993 | Fedorov et al. |
| 5,480,428 A | * | 1/1996 | Fedorov ............... A61F 2/1602 623/6.14 |
| 5,913,898 A | | 6/1999 | Feingold |
| 6,015,435 A | * | 1/2000 | Valunin ............... A61F 2/16 623/6.28 |
| 6,428,574 B1 | | 8/2002 | Valunin et al. |
| 6,706,066 B1 | | 3/2004 | Zhou et al. |
| 2003/0204253 A1 | | 10/2003 | Patel |
| 2004/0085511 A1 | | 5/2004 | Uno et al. |
| 2005/0125058 A1 | * | 6/2005 | Cumming ............ A61F 2/1613 623/6.37 |
| 2005/0149184 A1 | | 7/2005 | Bogaert |
| 2007/0162118 A1 | | 7/2007 | Rozakis et al. |
| 2009/0198326 A1 | | 8/2009 | Zhou et al. |
| 2011/0130831 A1 | | 6/2011 | Badawi et al. |

FOREIGN PATENT DOCUMENTS

| | | | |
|---|---|---|---|
| DE | 102004061943 A1 | 7/2006 | |
| WO | WO0130273 | * 3/2001 | ........... A61F 2/1602 |
| WO | WO 2002/003891 A1 | 1/2002 | |
| WO | WO 2014/167425 A1 | 10/2014 | |

OTHER PUBLICATIONS

Fechner, et al., "Posterior chamber myopia lens in phakic eyes", Journal of Cataract and Refractive Surgery, Mar. 1996, vol. 22, Issue 2, pp. 178-81, Abstract only, 2pgs.

Kawamorita, et al., "Fluid Dynamics Simulation of Aqueous Humor in a Posterior-Chamber Phakic Intraocular Lens with a Central Perforation", Graefes Arch Clin Exp. 1 Ophthalmol, Jun. 2012, vol. 250, Issue 6 pp. 935-939.

Koivula, A., et al., "Optical Coherence Tomography of the Anterior Segment in Eyes with Phakic Refractive Lenses", Ophthalmology, 2007, vol. 114, Issue 11, pp. 2031-2037, Abstract only, 2 pgs.

Perez-Combrodi, et al., "Preliminary in vivo positional analysis of a posterior chamber phakic intraocular lens by optical coherence tomography and its correlation with clinical outcomes", Journal of Optometry, Jul. 2012, vol. 5, pp. 121-130.

U.S. Appl. No. 14/661,262, filed Mar. 18, 2015, by Wilcox et al.

Canadian Office Action dated Jun. 11, 2018 for Application No. CA 2,980,142, 5 pgs.

Australian Office Action, Examination report No. 1 for standard patent application, dated Apr. 17, 2018 for Application No. AU 2016233337, 3 pgs.

International Search Report and Written Opinion for International PCT Application No. PCT/US2016/022545, dated Jun. 20, 2016, 12 pages.

Korean Office Action dated Dec. 19, 2018 for Application No. 10-2017-7029901, 6 pages.

Chinese Office Action dated Jan. 4, 2019 for Application No. 201680028713.6, 5 pages.

Chinese Office Action dated Aug. 30, 2019 for Application No. 201680028713.6, 7 pages.

Korean Office Action dated Sep. 18, 2019 for Application No. 10-2017-7029901, 5 pages.

* cited by examiner

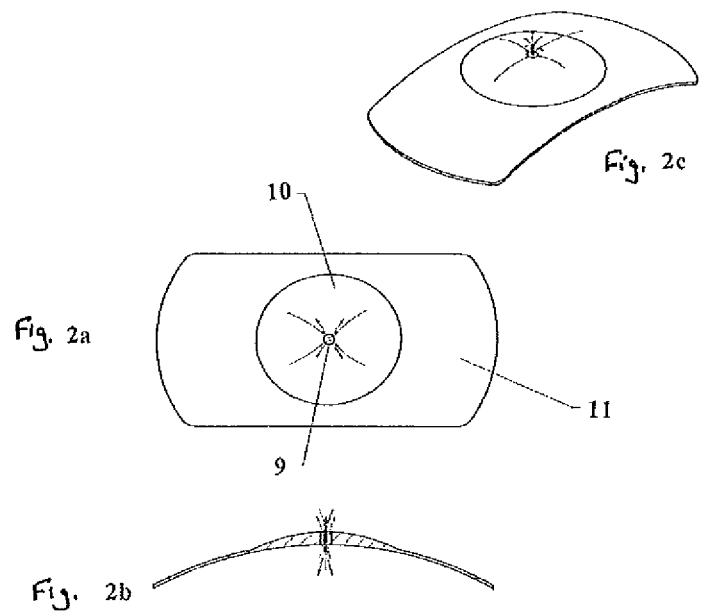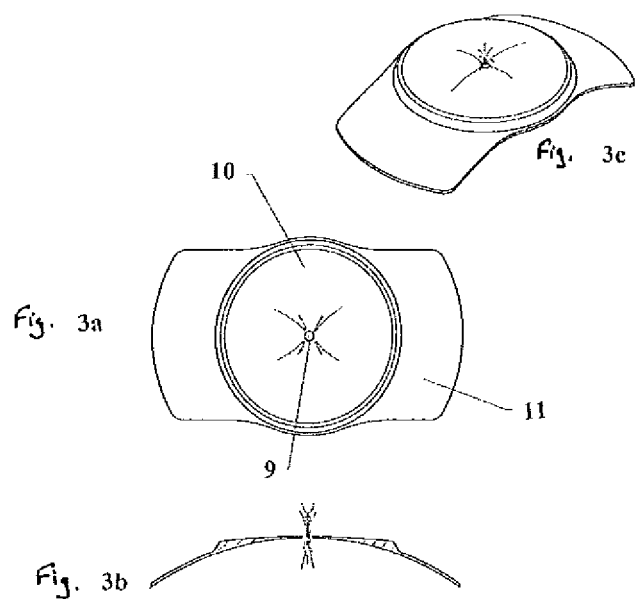

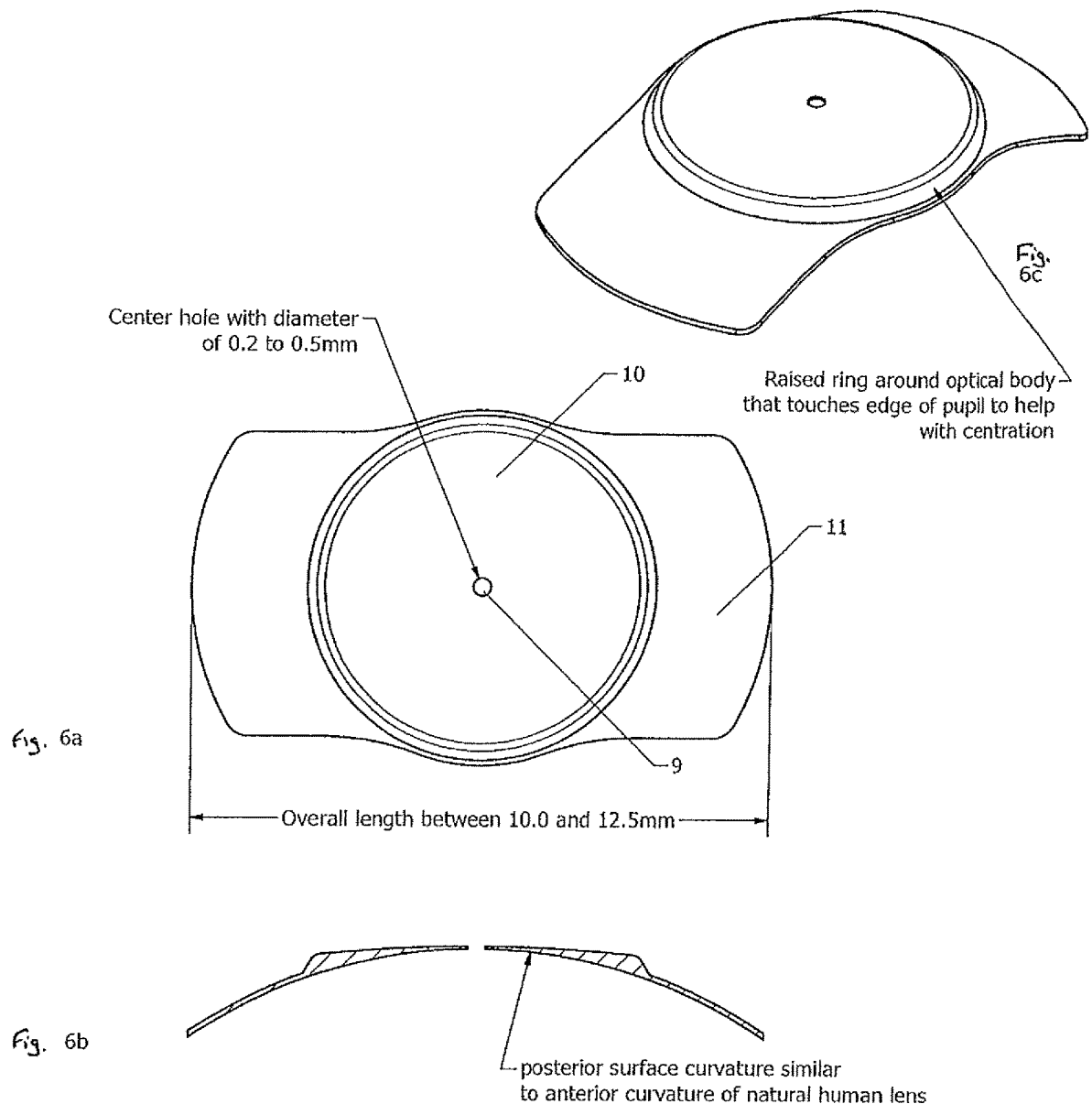

SELF-CENTERING PHAKIC REFRACTIVE LENSES WITH PARACHUTE DESIGN

TECHNICAL BACKGROUND

This application is a continuation-in-part of U.S. patent application Ser. No. 14/661,262, filed Mar. 18, 2015, incorporated by reference herein.

The present invention relates to intraocular lenses implanted into the eye for the correction of vision. When a lens is implanted in an eye that contains a natural crystalline lens, the implanted lens is a phakic lens. A phakic lens may be implanted into the anterior chamber, the area behind the cornea and in front of the iris, or into the posterior chamber that is behind the iris. A posterior chamber phakic refractive lens (PRL) is surgically implanted behind the iris and in front of the human natural crystalline lens for correcting ametropia or refractive errors, such as myopia and hyperopia. Implantation of a phakic refractive lens is the only reversible surgical procedure for correcting severe refractive errors in myopic and hyperopic patients. A number of possible complications have slowed the acceptance of this procedure. They are (1) intraocular pressure (TOP) elevation; (2) cataract induction; and (3) iris pigment dispersion. These complications have been linked to lens designs that are permanently fixed in the eye through attachment to anatomical structures such as the ciliary sulcus and iris.

A floating phakic refractive lens has been designed which preserves eye dynamics and greatly reduces the risk of these complications, especially compared to other phakic refractive lens designs. The floating design allows aqueous flow in the eye to reduce or eliminate the risk of intraocular pressure rise and reduces the chance of contact of the refractive lens with the natural crystalline lens that could induce a cataract or forced connection to the iris that causes iris pigment dispersion. A floating lens design has solved these serious problems by its ability to move with the dynamic changes in the eye, such as accommodation, but this freedom of movement can lead to decentration away from the optical center of the eye within the iris opening (pupil). Decentration can be associated with a rare but potentially serious complication, movement of the lens past the zonules and into the vitreous cavity behind the natural crystalline lens. The zonules are fibers connecting the ciliary process of the eye to the natural crystalline lens. In some people, especially those with very high degree of myopia or hyperopia, the zonules may become weakened and/or detached. If one side of a decentered floating phakic refractive lens, the tip of the haptic member, comes to rest on the zonules, loss of zonule integrity could allow the resting lens to slip through the gap. An additional surgical manipulation would then be required to retrieve the phakic refractive lens.

An improved method for centering the phakic refractive lens that preserves the benefits of that design and does not depend on problematic permanent fixation is needed.

There are a number of patents describing the posterior chamber phakic refractive lens concept and specific lens designs. U.S. Pat. No. 4,585,456, Blackmore, issued Apr. 29, 1986, discloses a phakic intraocular lens composed of flexible materials which is positioned against the natural lens of the eye and is held in place immediately adjacent to the natural lens and the ciliary sulcus. The lens is fixed in place, rather than floating. It assumes that stable centration is achieved by fixing the position of the lens through direct and constant contact with the tissues and structures of the eye. Intraocular pressure elevation and cataract formation are complications from such a lens design. These complications are documented by Fechner, et al, in the Journal of Cataract and Refractive Surgery, March 1996, Volume 22, pages 178-81. Even in a fixed lens that has a length matched to the diameter of the eye, which is difficult to achieve, the lens will eventually contact the natural lens, resulting in a subcapsular cataract. This is because the natural lens grows throughout life and will eventually press against the fixed refractive lens.

Other patents describe different ways of reducing intraocular pressure elevation and avoiding cataract formation by phakic refractive lens designs and their fixation mechanisms. Fedorov, in U.S. Pat. No. 5,480,428, issued Jan. 2, 1996, discloses a novel phakic lens design with an opening through the center of the optic body. This open hole allows aqueous humor to flow through the lens body, from its source in the posterior chamber to the anterior chamber of the eye. The hole is designed to restore aqueous flow and reduce intraocular pressure that builds when the lens body blocks the iris opening. The hole was also found to reduce the optical performance of the lens. Fedorov, in U.S. Pat. No. 5,258,025, issued Nov. 2, 1993, discloses that post-operative inflammation, caused by the supporting element's contact with ocular tissue, is prevented by moving supporting elements to the periphery of the phakic lens. The patent teaches that the Zinn's zonules are strong enough to hold the supporting elements in place without causing inflammation. Feingold, in U.S. Pat. No. 5,913,898, issued on Jun. 22, 1999, discloses an improvement of the Fedorov posterior chamber phakic refractive lens design with the supporting elements placed in the ciliary sulcus; the lens includes a hole in the center of the optic for equalizing pressure in the eye. These fixed designs are wide and span the inner diameter of the posterior chamber, effectively blocking the aqueous flow from the anterior chamber where it should exit the eye. The natural pressure equalizing mechanism has been compromised, effectively creating conditions that could lead to glaucoma. A hole in the lens allows the aqueous flow to be re-established. A number of later patent applications, such as Patel, US Published Application 2003/0204253, published Oct. 30, 2003, and Bogaert, US Published Application 2005/0149184, published Dec. 14, 2004, disclose holes or penetrating channels in the phakic lens body for the purpose of allowing aqueous flow that are said to prevent intraocular pressure increases. These are posterior chamber phakic lens designs that are fixed in place and use a hole in the optic body to reduce intraocular pressure that may lead to glaucoma.

Kawamorita et al, in "Fluid Dynamics Simulation of Aqueous Humor in a Posterior-Chamber Phakic Intraocular Lens with a Central Perforation", Graefes Arch Clin Exp Ophthalmol (2012), Volume 250: 935-939, discuss a computer model of the flow of aqueous humor through a hole in the center of the optic of a posterior chamber phakic refractive lens. The authors indicate that the hole was created to allow increased aqueous flow between the natural lens and phakic implanted lens and to equalize pressures in the eye. The analysis shows that aqueous humor is channeled through the center hole at a higher rate than the flow around the lens body. The analysis also showed that the flow velocity between the anterior surface of the natural crystalline lens and the posterior surface of the posterior chamber phakic lens is increased relative to the situation with the same phakic lens design without a center hole. In this case, the lens design includes fixation of the haptic members in the ciliary sulcus. In other words, the lens is not a floating design.

The floating phakic refractive lens design is disclosed in Valyunin, et al, U.S. Pat. No. 6,015,435, issued Jan. 18, 2000, and U.S. Pat. No. 6,428,574, issued Aug. 6, 2002. The floating lens design has an annular ring around the optic area, in the case of a lens for the correction of myopia, or a protruding optic, in the case of a lens designed for treatment of hyperopia, that comes in contact with the edge of the iris, the iris thereby applying a centering force to the lens. A haptic member is attached to the optic that is designed to prevent the optic from being grossly decentered away from the pupil. The haptic is designed with a curvature substantially equivalent to the curvature of the natural lens (see FIG. 1 and FIG. 6 of Valyunin). This floating lens design works with the iris to channel aqueous flow around the lens to reduce the risk of intraocular pressure rise and help to maintain a gap between the implant and the natural lens. The floating behavior of the lens is further assured by matching the material properties of the lens to the aqueous medium of the eye, disclosed in U.S. Pat. No. 6,706,066, Zhou et al, issued Mar. 16, 2004. The specific gravity and mass per unit surface area of the phakic lens material are combined with the phakic lens design to cause the lens to float in the eye and allow the eye dynamics to help maintain the position and centration of the phakic refractive lens. Koivula, et al, in Opthalmology (2007), Volume 114, pages 2031-2037, used optical coherence tomography imaging to show that such a lens moves with the natural eye dynamics to allow a normal aqueous humor flow inside the posterior chamber.

Perez-Cambrodi, et. al., in the Journal of Optometry July 2012, Volume 5, pages 121-130, found, in an analysis of a series of patients implanted with floating phakic refractive lens, that there was contact between one of the haptic members and the zonules in some cases. Positional analysis indicated a trend toward nasal decentration. This did not have a significant effect on the performance of the phakic refractive lens, but continued contact of the phakic refractive lens with the zonules could eventually lead to the complication of zonular dehiscence and dislocation of the lens toward the vitreous chamber (the back of the eye near the retina). Adding an additional design feature that could preserve a floating feature could have significant patient benefits while improving centration of the lens would be a significant improvement, further reducing risks associated with an anatomically compatible phakic refractive lens designed to restore emmetropia in myopic or hyperopic human eyes.

BRIEF SUMMARY

The current invention provides a posterior chamber floating phakic refractive lens, with particular lens design and materials, that may be placed in the posterior chamber of the human eye for correction of refractive errors. This invention also provides a phakic refractive lens that can float in aqueous humor and that is flexible and soft. The floating action of the thin, rectangular, buoyant lens will help preserve the eye dynamics so that risks of cataract induction of the human crystalline lens, iris pigment dispersion and intraocular pressure increase are significantly reduced as complications of the implantation of a phakic refractive lens. The present invention uses a small center hole added to the lens optic to cause aqueous flowing through the hole to exert a centering force to the floating phakic refractive lens while preserving optical function. A floating lens design is the only design able to make use of aqueous medium flowing through a central hole to help achieve a stable centration of the optic and to help move the optic body into the pupillary space, maintaining the gap between the phakic refractive lens and the natural crystalline lens.

As used herein, all percentages and ratios are "by weight", unless otherwise specified. In addition, all patents, patent applications and publications cited herein are incorporated herein by referenced.

DESCRIPTION OF THE DRAWINGS

FIG. 2 includes a top view (FIG. 2a), side view (FIG. 2b) and perspective view (FIG. 2c) of the lens of the present invention intended for treatment of hyperopia, including arrows that show aqueous flow through the central hole (9). In these figures, 10 is the optic or optical body and 11 is the haptic.

FIG. 3 includes a top view (FIG. 3a), side view (FIG. 3b) and a perspective view (FIG. 3c) of the lens of the present invention intended for treatment of myopia, including arrows that show aqueous flow through the central hole, FIG. 4 includes a top view (FIG. 4b) and side view (FIG. 4a) of a prior art fixed position intraocular lens where haptic members fix the lens position through contact with tissues of the eye, FIG. 5 includes top views (FIGS. 5a, 5b and 5c) of three prior art fixed position intraocular lenses. 7 indicates a feature that fixes the lens position through attachment to the iris. Item 8 indicates a lens design feature that fixes the lens position in the eye through fixation with the tissue of the ciliary sulcus.

FIG. 6 includes a top view (FIG. 6a), side view (FIG. 6b) and perspective view (FIG. 6c) of a lens of the present floating lens invention designed for the treatment of myopia that includes some description of the design.

DETAILED DESCRIPTION

Figure 1:
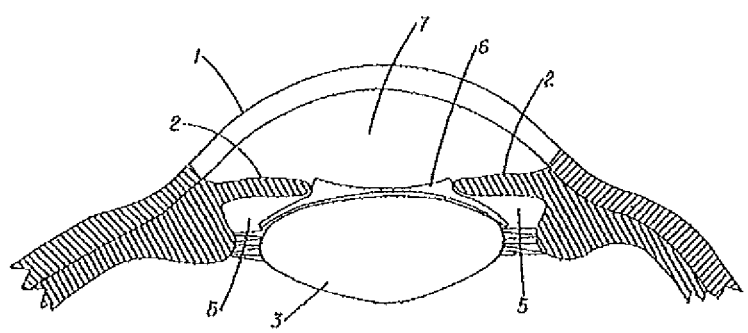
FIG. 1 is a cut-away view of the eye showing the positioning of the lens of the present invention. The cornea, the front surface of the eye, is reference no. 1. The iris is seen at 2. The natural crystalline lens is 3. The posterior chamber is item 5 and the anterior chamber of the eye is 7. The phakic intraocular lens of the present invention is 6.
Figure 4B:
Figure 4A:
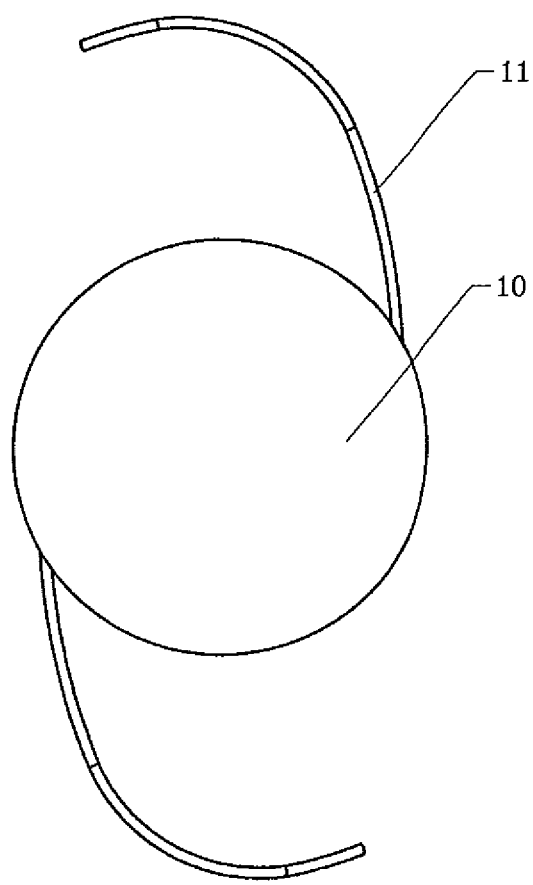
Figure 5A:
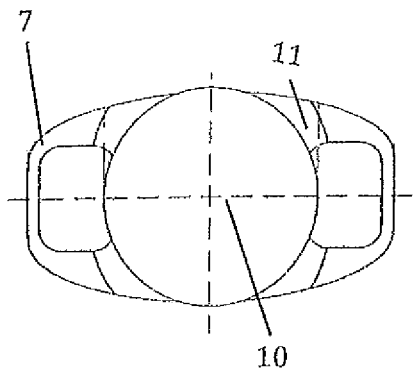
Figure 5B:
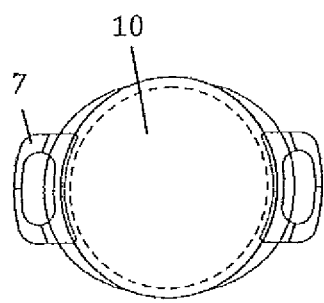
Figure 5C:
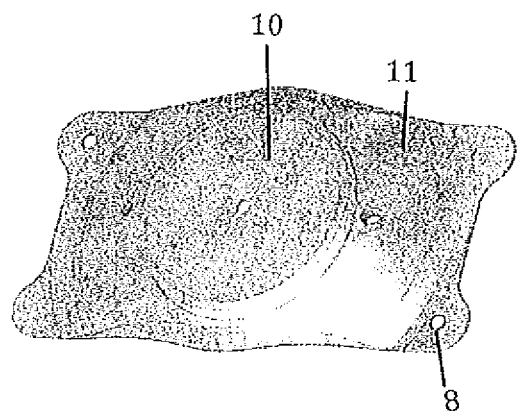

The present invention is a specific lens design improvement meant to solve problems with prior art phakic refractive lens designs by using the existing dynamics of the eye, including the ever-present aqueous flow and accommodation mechanisms, to assist with centering the floating phakic refractive lens, making it a more effective treatment for refractive errors. A floating phakic refractive lens is made with materials that have a specific gravity (e.g., from about 0.9 to about 1.2 g/cm$^3$) near the specific gravity of the aqueous humor of the eye. This will allow buoyant floating of the lens, particularly because the design, disclosed in U.S. Pat. No. 6,015,435, Valyunin et. al., issued Jan. 18, 2000, incorporated herein by reference, includes one or more thin haptic members extending from the optic that are in a rectangular airfoil-like shape similar to the shape of a modern, rectangular parachute. This gives the top view of the lens a generally rectangular shape (see FIG. 2a). Continuing the parachute analogy, the history of parachute design shows that violent swaying and oscillating motions were a characteristic of early parachutes without a central vent hole. The flowing surrounding medium (whether air or water) behind the center canopy, which would correspond to the optic zone for a floating phakic refractive lens, could spill around alternating sides of the canopy, causing severe oscillatory movement. A vent hole in the center of the canopy or optic produces a vertical stream of fluid that suppresses eddy currents and stabilizes the position of the parachute or parachute-like lens. Experience has shown that a circular parachute with a central vent hole is more stable than a parachute without the hole but positional stability and control of final landing position are still not optimal with a purely round canopy. Improvements in stability and precise control of parachute movement have been made by moving to rectangular parachute designs.

The rectangular design helps a parachute float in the surrounding medium in a more stable fashion than a purely circular design; fluid that flows around the edges of the rectangle help prevent destabilizing eddy currents. The rectangular design can be maneuvered more precisely as it responds smoothly to changes in flow direction of the surrounding medium that could be affected by the parachutist. A shape with a high aspect ratio, defined as a design which is longer than it is wide, is known in nature and aeronautical science to give an increased amount of lift. Using an aspect ratio in a range between about 1.4 and about 2.0 (length divided by width) results in a stable, maneuverable parachute that is preferred for precision formation parachute flying and landing. The lens design disclosed in U.S. Pat. No. 6,015,435 (Valyunin et. al.) and U.S. Pat. No. 6,706,066 (Zhou et. al.), both incorporated by reference herein, has an aspect ratio in that range and bears a resemblance to such a rectangular parachute but the preferred embodiment of the invention in those patents did not include a hole in the center of the optic body as it was not needed for a floating lens design to equalize pressure in the eye or to prevent a suction force that caused the phakic lens to attach to the natural crystalline lens, as in the case of the Fedorov design disclosed in U.S. Pat. No. 5,258,025. See also U.S. Published Patent Application 2007/0162118, Rozakis et al, published Jul. 12, 2007, incorporated herein by reference.

The phakic refractive lens design of the present invention floats in an aqueous medium that is not static but flowing around the lens body, like a parachute in flight, with a flow from the choroid in the posterior chamber, through the pupil and into the anterior chamber. The aspect ratio of the floating lens design is between about 1.4 and about 2.0, similar to the stable, maneuverable parachute designs used for precision formation flying, even under windy conditions. The floating behavior is further enhanced by the material used to make the thin, rectangular lens. The material is designed to have a specific gravity close to the surrounding aqueous medium so that the lens can be buoyant and float within the aqueous medium (e.g., a specific gravity between about 0.9 and about 1.2 g/cm$^3$). The lenses of the present application can be made from materials which can be hydrophilic or hydrophobic, have the desired optical properties, and are foldable with quick shape recovery, and include, for example, silicone polymers, poly(acrylates), poly(methacrylates), hydrogels, proteins, collagens, copolymers, and mixtures thereof. The materials typically have a hardness of from about 20 to about 60 Shore A.

The lens herein includes a hole in its central portion. The hole is generally from about 0.2 to about 0.5 mm in diameter, such as about 0.35 mm in diameter. The hole is located in the central portion of the optic body; it can be located at the true center of the optic, or the center of the hole can be located within a 0.2 mm diameter circle defined from the true center of the optic body. Typically, only a single hole is used. Multiple holes raise the risk of reduced optical quality. The overall length of the lens of the present invention (i.e., from haptics end to haptics end is from about 10 mm and about 12.5 mm).

With the lens floating in the posterior chamber of the eye, design features have been added to encourage movement of the lens towards the center of the pupil. The lens design with a negative curvature for the treatment of myopia includes a raised ring around the optic that has a smooth, rounded shape. The lens with a positive curvature on the anterior side has an optic zone that extends out with a gentle curve from the level of the haptic members. These protrusions will be captured by the edge of the iris opening. When the eye is exposed to light and the iris closes to adjust the amount of light (i.e. the pupil becomes smaller in diameter), the lens body is moved towards the center of the pupil. In this way, the optic area is designed to be captured by the iris, helping to keep the lens floating towards the optical center of the eye.

A weakness of depending solely on this centration mechanism is that the pupil of some individuals may open to 6 mm or more in diameter in the dark or when sleeping. The lens body could be allowed to move towards one of the zonules, the fibers suspending the natural lens in the eye. Analysis of the phakic refractive lens design in the light of studies on the aqueous flow within the eye suggests that positional stability and centration of the lens could be improved by adding another feature that used the existing fluid dynamics of the eye. Richard F. Brubaker, in his Friedenwald Lecture, "Flow of Aqueous Humor in Humans", teaches that aqueous homor is continuously being transported into the posterior chamber of the eye through ciliary epithelial cells. The aqueous humor flows through the pupil into the anterior chamber at an approximate mean rate of 2.75±0.63 µl/minute in normal human subjects, circulates around the anterior chamber, and exits through various mechanisms. Kawamorita et. al. investigated the fluid dynamic characteristics of aqueous humor in a phakic refractive lens with a hole in the center of the optical body using computational fluid dynamics. Using the aqueous humor flow values described in Brubaker, they found a significant increase in flow velocity between the anterior surface of the natural lens and the center of the posterior surface of the refractive lens around the hole, with a sharp flow rate increase of 0.15 mm/second in the center of the hole. Trajectory analysis showed aqueous humor flow through the hole and into the anterior chamber. Practical experience with a hose nozzle shows that water accelerates when pushed through a narrow hole. Consideration of the eye's aqueous flow dynamics described by Brubaker and the computer model of aqueous flow through a center hole of a phakic refractive lens by Kawamorita et al suggests that a central hole in the optic body of a floating phakic refractive lens could be a centering feature. A central vent hole added to the floating lens design, as it was to parachute designs, improves the centration and position stability of the lens in the flowing aqueous medium. Another benefit of this improved design element is that the slight acceleration of the flow through the hole would tend to move or lift a floating lens in the direction of the center of the pupil, like a parachute opening in a column of air. This could possibly increase or help maintain the gap between the floating lens and the natural crystalline lens, further reducing the risk of the floating lens touching the natural lens. In addition, this gap is maintained by the fact that the posterior surface curvature of the present lens is similar to the anterior curvature of the natural human lens. The floating phakic refractive lens has been designed to reduce the risk for complications such as increased intraocular pressure, pigment dispersion, secondary cataract, and loss of endothelial cells compared to other phakic refractive lens designs. The addition of the hole in the optical body of the present invention to help centration of the refractive lens is a significant improvement for a safe and effective treatment for refractive errors, such as myopia and hyperopia, that affect millions of people.

The phakic intraocular lens of the present invention is useful for correcting ametropia or refractive errors, such as myopia and hyperopia. It is also useful for treating presbyopia, the condition where older adults have difficulty with near vision and reading because of the natural aging of the human crystalline lens. Specifically, the natural lens begins to lose its ability to move and change shape during the natural process of accommodation. Accommodation is the process where the eye (and brain) changes focus between long distance, intermediate and near vision. As the natural lens gets older, it loses some of its ability to make this change in focus, resulting in presbyopia (also called dysfunctional lens syndrome). The phakic refractive lens of the present invention having a low positive power (such as from about +0.0 (e.g., +0.1) to about +3.0 Diopters) will help people who have presbyopia and, as a result, have difficulty with reading close and especially small type, without requiring reading glasses. Additionally, the phakic refractive lens having a low positive power, in the range of +4.0 to +10.0 Diopters (e.g., about 6.0 Diopters), and an optic diameter of less than about 3 mm (e.g., about 1-2 mm), can also act as an image magnifying lens to aid people with conditions that affect retinal function, such as macular degeneration and retinitis pigmentosa.

EXAMPLES

The following examples are given for the purpose of illustrating the present invention and are not intended to be limiting thereof.

Example 1—Floating Silicone Phakic Refractive Lens (Prior Art)

A small amount of a two-part silicone material with a specific gravity between 0.95 and 1.05 is mixed at a 10:1 ratio and placed in a metal mold. The mold is clamped shut and placed in a curing oven at 120° C. for 70 minutes. The mold is cooled to room temperature, opened, and the phakic lens is carefully removed. The phakic lens has the configuration and dimensions of the lens in FIG. 1.

The lens is placed in a container with water and the lens can be seen to float on the top of the water. If forced under the water surface, the lens remains floating under the surface. If a stream of moving water is caused to flow under the floating lens, the lens returns to the surface. The lens movement is uncontrolled, with occasional movements towards the side of the container or exaggerated rocking movements.

Example 2—Floating Silicone Phakic Refractive Lens with Center Hole

A small amount of a two-part silicone material with a specific gravity of 0.95 to 1.05 is mixed at a 10:1 ratio and placed in a metal mold. The mold is clamped shut and placed in a curing oven at 120° C. for 70 minutes. The mold is cooled to room temperature, opened, and the phakic lens is carefully removed. A hole with a diameter of approximately 0.4 mm is made in the center of the optic. The phakic lens has the configuration and dimensions of the lens in FIG. 6.

The lens is placed in a container with water and the lens can be seen to float on the top of the water. If forced under the water surface, the lens remains floating under the surface. If a stream of moving water is caused to flow under the floating lens, the lens returns to the surface. The lens movement is more controlled than the lens with no hole in the center; the lens rises vertically and the lens orientation is conserved.

Example 3—Floating Silicone Phakic Refractive Lens with Center Hole

The phakic refractive lens of Example 2 is evaluated for optical performance and compared to the optical performance of the lens of Example 1 that has no hole in the center of the optic. A commonly used method for evaluating optical performance is to place the lens on an optical bench with a collimator, objective lens, and a US Air Force 1951 Target or similar target image. The ability of the test lens to completely and clearly resolve an image pattern such as a group of closely spaced lines or bars is evaluated as a measure of resolution efficiency and imaging quality. Another measure of imaging quality and optical performance is the modulation transfer function (MTF). It is found that when the center hole is between 0.2 and 0.5 mm in diameter, there is no significant difference in optical performance between the lenses of Example 1 and Example 2.

What is claimed is:

1. An anatomically compatible phakic refractive intraocular lens designed to float in an aqueous humor within a posterior chamber of an eye, between an iris and a natural crystalline lens of the eye, said phakic refractive lens comprising:
   a. an optical body having a diameter of from about 3 mm to about 7 mm;
   b. one or more haptic members that extend from the optical body to give an overall length between about 10.0 mm to about 12.5 mm;
   c. wherein the phakic refractive lens is designed such that a posterior surface of the phakic refractive lens conforms in whole to a shape of an anterior surface of the natural crystalline lens; and
   d. a hole or fenestration in an approximate center of the optical body, said hole or fenestration having a diameter between about 0.2 and about 0.5 mm, for the purpose of allowing aqueous flow through the hole or fenestration that acts to improve centration of the floating phakic refractive lens;
   wherein the phakic refractive intraocular lens has a specific gravity between about 0.9 and about 1.2 g/cm$^3$, an anterior face of the phakic refractive lens includes a design feature which encourages movement of the phakic refractive lens toward a center of a pupil of the eye and wherein the design feature is a raised ring around the optical body, or a positive curvature on the anterior face of the phakic refractive lens, either of these design features being protrusions which interact with an opening of the iris.

2. The phakic refractive lens according to claim 1 made from a hydrophobic material.

3. The phakic refractive lens according to claim 1 made from a hydrophilic material.

4. The phakic refractive lens according to claim 1 made from a material selected from the group consisting of silicone polymers, poly(acrylates), poly(methacrylates), hydrogels, proteins, collagens, copolymers, and mixtures thereof.

5. The phakic refractive lens according to claim 1 wherein the phakic refractive lens comprises materials having a hardness of about 20 to about 60 Shore A.

6. The phakic refractive lens according to claim 1 wherein the phakic refractive lens has a generally rectangular shape.

7. The phakic refractive lens according to claim 6 wherein the generally rectangular shape has an aspect ratio between about 1.4 and about 2.0.

8. The phakic refractive lens according to claim 1 wherein a power of the lens may be defined by an anterior surface of the optical body and/or a posterior surface of the optical body.

9. A method for correcting the vision of a patient by inserting into the posterior chamber of the eye of said patient, between the patient's iris and the patient's natural crystalline lens, an anatomically compatible phakic refractive intraocular lens comprising:
  a. an optical body;
  b. one or more haptic members that extend from the optical body;
  c. a posterior surface, wherein the posterior surface has a shape conforming in whole to a shape of an anterior surface of the natural crystalline lens of the eye;
  d. an anterior surface having a design feature comprising a protrusion, wherein the design feature:
    1. is selected from the group of: a raised ring around the optical body, a positive curvature on the anterior surface and combinations thereof; and
    2. the protrusion of the design feature interacts with an opening of the iris to encourage movement of the phakic refractive intraocular lens toward a center of a pupil of the eye, wherein the design feature; and
  e. a hole or fenestration in the approximate center of the optical body.

10. The method according to claim 9 wherein a condition being corrected is presbyopia.

11. The method according to claim 10 wherein the phakic refractive lens has a low positive power.

12. The method according to claim 11 wherein the phakic refractive lens has a power of from about +0.0 to about +3.0 Diopters.

13. The method according to claim 9 wherein the phakic refractive lens has a power of from about +4.0 to about +10.0 Diopters, and an optic diameter of less than about 3 mm, and the condition being treated is a condition that affects retinal function.

14. The method according to claim 9 wherein the condition is macular degeneration or retinitis pigmentosa.

15. An anatomically compatible phakic refractive intraocular lens designed to float in an aqueous humor within a posterior chamber of an eye, between an iris and a natural crystalline lens of the eye, said phakic refractive intraocular lens comprising:
  f. an optical body;
  g. one or more haptic members that extend from the optical body;
  h. a posterior surface, wherein the posterior surface has a shape conforming in whole to a shape of an anterior surface of the natural crystalline lens of the eye;
  i. an anterior surface having a design feature comprising a protrusion, wherein the design feature:
    3. is selected from the group of: a raised ring around the optical body, a positive curvature on the anterior surface and combinations thereof; and
    4. the protrusion of the design feature interacts with an opening of the iris to encourage movement of the phakic refractive intraocular lens toward a center of a pupil of the eye, wherein the design feature; and
  j. a hole or fenestration in the approximate center of the optical body.

* * * * *